United States Patent [19]
Williams

[11] Patent Number: 6,006,137
[45] Date of Patent: Dec. 21, 1999

[54] METHOD FOR SINGLE ELECRODE BI-ATRIAL PACING

[75] Inventor: Terrell M. Williams, Brooklyn Park, Minn.

[73] Assignee: Medtronic, Inc., Minneapolis, Minn.

[21] Appl. No.: 09/036,114

[22] Filed: Mar. 6, 1998

[51] Int. Cl.⁶ ............................................. A61N 1/05
[52] U.S. Cl. ........................ 607/119; 607/122; 600/585
[58] Field of Search .................... 607/119, 122, 607/123, 125–128; 600/585, 374, 375

[56] References Cited

U.S. PATENT DOCUMENTS

| | | |
|---|---|---|
| 4,106,512 | 8/1978 | Bisping . |
| 4,257,428 | 3/1981 | Barton et al. . |
| 4,467,817 | 8/1984 | Harris . |
| 4,475,560 | 10/1984 | Tarjan et al. . |
| 4,497,326 | 2/1985 | Curry . |
| 4,646,755 | 3/1987 | Kane . |
| 5,188,606 | 2/1993 | Maloney et al. . |
| 5,487,385 | 1/1996 | Avitall ..................................... 600/374 |

FOREIGN PATENT DOCUMENTS

| | | |
|---|---|---|
| 0714671 | 6/1996 | European Pat. Off. . |
| 2132895 | 7/1984 | United Kingdom ................... 607/123 |
| 9308871 | 5/1993 | WIPO . |
| 9515115 | 6/1995 | WIPO . |

OTHER PUBLICATIONS

U.S. Patent Application SN 08/846008, "Medical Lead Connector System" filed Apr. 25, 1997 by Bischoff et al. Now U.S. Patent 5843141, Dec. 1, 1998 issued.

U.S. Patent Application SN 08/613298 "Method and Apparatus for R–F Ablation" filed Mar. 11, 1996. Now U.S. Patent 5755760, May 26, 1998 issued.

*Primary Examiner*—William E. Kamm
*Assistant Examiner*—George R. Evanisko
*Attorney, Agent, or Firm*—Reed A. Duthler; Harold R. Patton

[57] ABSTRACT

An atrial lead system and a method of employing it to provide a single electrode bi-atrial pacing. The system includes an atrial pacing lead having an electrode located on a distal portion thereof and a guide catheter having a longitudinal lumen and a lateral aperture open to the longitudinal lumen of the catheter proximal to a distal end of the catheter through which the distal portion of the lead may be advanced. The electrode is preferably an active fixation electrode or is associated with an active fixation device. The system is employed by first advancing the guide catheter to the ostium of a patient's coronary sinus and inserting the distal end of the guide catheter into the coronary sinus such that the lateral aperture of the catheter is located in the patient's right atrium. The atrial pacing lead is then advanced through the lumen of the guide catheter such that the electrode exits the lateral aperture of the guide catheter and the electrode is affixed to the tissue of the atrial septum.

9 Claims, 4 Drawing Sheets

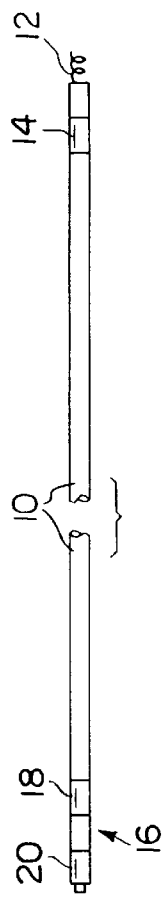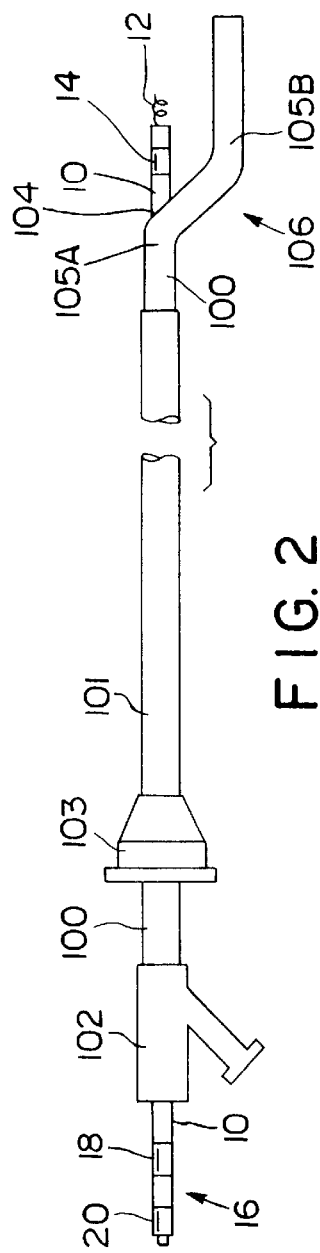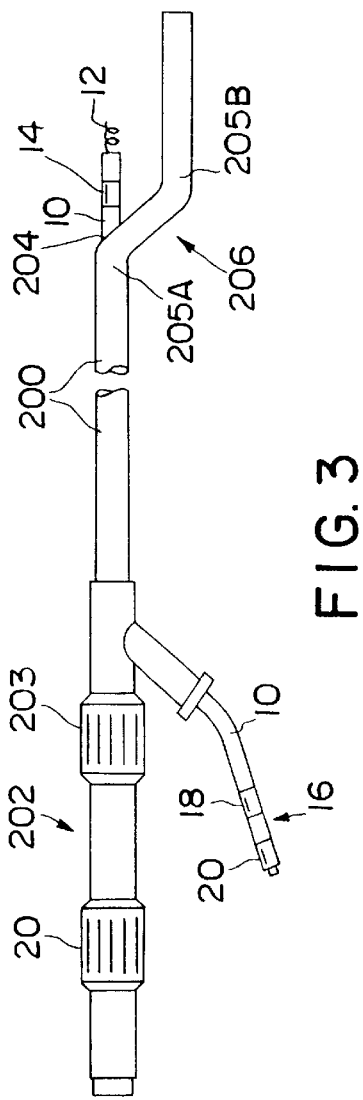

METHOD FOR SINGLE ELECRODE BI-ATRIAL PACING

BACKGROUND OF THE INVENTION

This invention relates generally to implantable medical leads, and more particularly to cardiac pacing leads and methods of their delivery. As discussed in the article, "Atrial Septal Pacing: A method for Pacing Both Atria Simultaneously", by Spencer et al. published in PACE, Vol. 29, November, 1997, pp. 2739–2745, it is possible to pace both atria with a single active fixation electrode appropriately located in the anterior portion of the right side of the atrial septum separating the right and left atria. However, using present lead technologies, accurate placement of a lead at this desired site, typically located adjacent and slightly above and anterior to the ostium of the coronary sinus can be relatively difficult. While delivery of cardiac pacing leads or other electrode catheters to desired locations within the heart by means of a deflectable or pre-curved guide catheter is known, typically the location of the lead to be so delivered must be determined flouroscopically. As the lead is to be placed while the heart is beating, placement even using a guide catheter is not as simple as would be desired.

SUMMARY OF THE INVENTION

The present invention is directed toward providing a reliable and easy to use mechanism for accurately locating an atrial pacing electrode in the atrial septum, adjacent and above the ostium of the coronary sinus. The present invention accomplishes this desired result by means of an active fixation atrial pacing lead delivered by means of a pre-curved or preferably a deflectable guiding catheter. The guiding catheter is provided with an internal lumen through which the atrial pacing lead is passed, which lumen exits laterally, proximal to the distal tip of the catheter. The distal portion of the catheter is pre-curved or deflectable into an S-shaped bend, having two generally coplanar curves, with a lateral exit aperture located along the outer portion of the more proximal of the two curves. The guiding catheter when so curved is configured so that when the distal tip of the guiding catheter is located in the coronary sinus, the distal end of the atrial lead may be advanced out of the lateral aperture of the guide catheter and embedded in the atrial septum at the desired location. Locating the distal end of the guide catheter in the coronary sinus both assists in proper location of the atrial pacing lead relative to the coronary sinus and in providing a stable platform, allowing the lead to be maintained in its desired location during the measurement of pacing and sensing thresholds and during placement of the electrode in the atrial septal tissue. After the atrial electrode is placed, the guide catheter is withdrawn over the lead, and the lead is coupled to an implantable cardiac pacemaker.

In a preferred embodiment, the guide catheter is configured so that it may be deflectable to first display only the more distally located of the two curves, facilitating placement of the guide catheter in the coronary sinus. The catheter then preferably may then be curved to also display the more proximal of the two curves, facilitating the exit of the atrial pacing lead adjacent to the desired location on the atrial septum. The catheter may be deflectable by any of the numerous presently known mechanisms for providing controlled variable curvature, including but not limited to the use of internal pull wires and the use of nested straight and pre-curved catheter tubes.

BRIEF DESCRIPTION OF THE DRAWINGS

FIG. 1 is a plan view of an atrial pacing lead appropriate for use in conjunction with the present invention.

FIG. 2 is a plan view of the lead of FIG. 1 in conjunction with a deflectable guide catheter according to a first embodiment of the present invention.

FIG. 3 is a plan view of the lead according to FIG. 1 in conjunction with a deflectable guide catheter according to a second embodiment of the present invention.

DETAILED DESCRIPTION OF THE PREFERRED EMBODIMENTS

Figure 5:
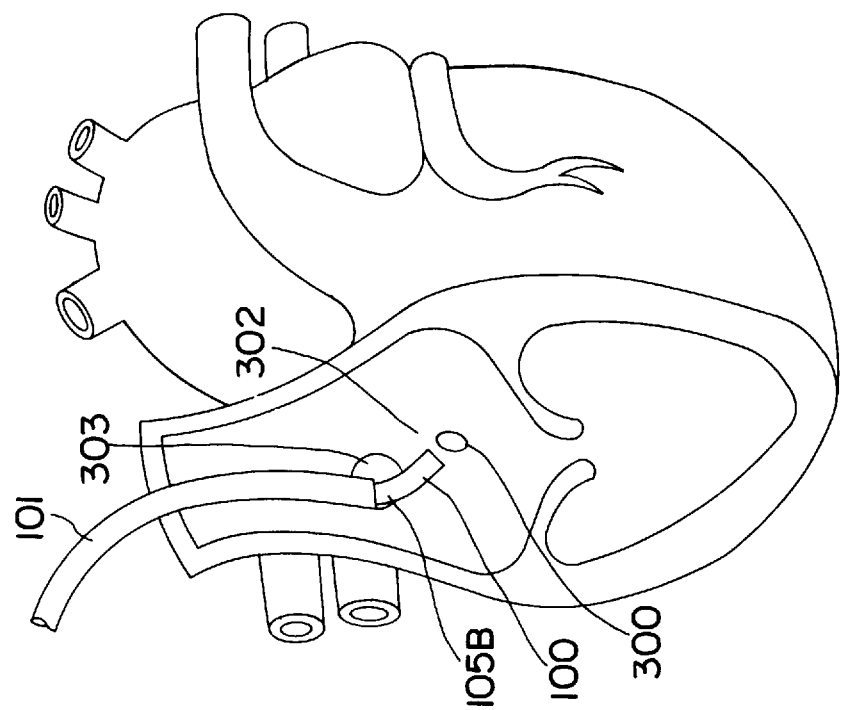
FIG. 5 illustrates the guide catheter of FIG. 2, deflected to display only the more distal of its two curves, prior to placement of the distal end of the guide catheter into the coronary sinus.

FIG. 1 illustrates an atrial lead according to the present invention. The lead is provided with an elongated insulative lead body 10 which carries at least one electrical conductor therein. As illustrated, the lead is configured as a bipolar lead and thus carries two conductors within lead body 10. Located at the distal end of the lead is an active fixation electrode 12 which in this case takes the form of a helical electrode. An optional, indifferent electrode 14 is provided proximal to the active fixation electrode 12. Electrode 12 as illustrated takes the form of a fixed helix, rotatable into body tissue by rotation of lead body 10. Alternatively, electrode 12 may be replaced with an advanceable helix as disclosed in U.S. Pat. No. 4,106,512 issued to Bisping or may take the form of a barb, hook or other known type of active fixation electrode as described in U.S. Pat. No. 4,497,326 issued to Curry, U.S. Pat. No. 4,257,428 issued to Barton et al. or U.S. Pat. No. 4,475,560 issued to Tarjan et al., all of which are incorporated herein by reference in their entireties. As an additional alternative, electrode 12 may be replaced by a ring or tip electrode in conjunction with a separate active fixation device, if desired.

At the proximal end of the lead is located an iso-diametric connector assembly 16 which carries two connector rings 18 and 20, coupled to electrodes 14 and 12, respectively by means of conductors located in lead body 10. Iso-diametric connector 16 may correspond to that in allowed, commonly assigned, U.S. patent application Ser. No. 08/846,008 by Ries et al., filed on Apr. 25, 1997, now U.S. Pat. 5,843,141 also incorporated herein by reference in its entirety. The provision of an iso-diametric connector assembly is believed beneficial in the context of the present invention in that it simplifies removal of the guide catheter over the lead body by simply pulling the guide catheter proximally over the lead. In the absence of an iso-diametric connector assembly, provision for splitting or slitting the guide catheter to enable its removal over the connector assembly as disclosed in U.S. Pat. No. 5,188,606, issued to Maloney et al., incorporated herein by reference in its entirety could alternatively be provided.

FIG. 2 illustrates the lead of FIG. 1 mounted in a guide catheter according to the present invention. The guide catheter is provided with an elongated, pre-curved catheter body comprised of a curved inner tube 100 and a straight outer tube 101. The longitudinal lumen within tube 100 exits at a lateral aperture 104 through which the distal portion of the lead of FIG. 1 can be seen emerging, with electrodes 12 and 14 visible exterior to the guide catheter tube 100. At the proximal end of catheter tube 101 is a fitting 103, through which catheter tube 100 exits. At proximal end of catheter tube 100 is a fitting 102, through which lead body 10 exits. The proximal portion of the lead body 10, connector assembly and connector rings 18 and 20 are visible exiting the proximal end of fitting 102.

Lead body 10 is slidable within tube 100 so that its distal end may be drawn proximally into tube 100 through lateral aperture 104. Tubes 100 and 102 are similarly slidable relative to each other so that the distal, curved portion 106 of tube 100 may be drawn into the distal end of tube 101, thereby straightening tube 100 to provide a guide catheter with a generally straight configuration. The curved portion of tube 100 is provided with two generally planar oppositely directed curves 105A and 105B. In the embodiment illustrated, curve 105B is located about an inch proximal to the distal end of tube 100 and curve 105A is located about ⅜ of an inch proximal to curve 5B. Both curves in the embodiment illustrated are about 45 degrees. Lateral aperture 104 is located on the outside of curve 105A, axially aligned with the portion of catheter tube 100 extending proximal thereto, facilitating exit of the distal end of the lead body 10 an rotation of lead body 10 to screw electrode 12 into heart tissue.

Initially, lead body 10 is withdrawn into tube 100 and tube 100 is withdrawn into tube 101 to provide a generally straight guide catheter. When the distal end of the guide catheter enters the right atrium, tube 100 is advance distally relative to tube 101 to allow curve 105B to exit tube 101, providing a guide catheter with a single curve configured to assist in location of the distal end of the guide catheter in the coronary sinus. After the distal end of the guide catheter is in the coronary sinus, tube 101 is withdrawn proximally to allow curve 105A to exit tube 101, and the distal end of lead body 10 is then advanced distally through lateral aperture 104 and screwed into the inter-atrial septum. The guide catheter is then withdrawn proximally over lead body 10.

FIG. 3 illustrates the lead of FIG. 1 in conjunction with an alternative, deflectable guide catheter according to the present invention. The guide catheter as illustrated employs two internal deflection wires to provide two curves 205 and 205B, corresponding to curves 105A and 105B illustrated in FIG. 2. At the proximal end of the catheter body 200 is a handle 202 which carries two rotatable knobs 201 and 203, each of which pulls one of the two tension wires within the catheter body 200, for example using the mechanisms disclosed in allowed U.S. patent application Ser. No. 08/613,298 filed by Maguire et al. on Mar. 11, 1996, now U.S. Pat. No. 5,755,760 and incorporated herein by reference in its entirety. One deflection wire extends to a point just distal to curve 205A and the other extends to a point distal to curve 205B and, in the manner described in the Maguire et al. application, may be employed to cause the catheter body 200 to successively display curves 205B and 205A, allowing the guide catheter to perform in a manner analogous to the guide catheter illustrated in FIG. 2. Like the guide catheter of FIG. 2, the guide catheter is provided with a lateral aperture 204 which is located on the exterior of curve 205A. The proximal end of lead body 10, carrying connector assembly 16 is shown exiting the handle 202.

Preferably, the length of the lead of FIG. 1 is sufficient so that the connector assembly 16 and the proximal portion of the lead body 10 extend proximal to the handle or fitting of the guide catheters of FIGS. 2 and 3 when the electrode 12 is located in or adjacent the tissue of the atrial septum, to allow for connection of the electrode connectors 18 and 20 to an external pacing systems analyzer to facilitate the taking of pacing and sensing thresholds, before and after placement of electrode 12 and to allow rotation of lead body 10 to screw electrode 12 into atrial tissue. As illustrated, the lateral aperture 104 is shown exiting on the interior of the curve either preformed into the guide catheter as in FIG. 2 or formed by tension applied to the internal pull wires in the catheter of FIG. 3. This in turn facilitates location of the electrode 12 in the atrial septal tissues above the ostium of the coronary sinus when the distal ends of the catheter bodies 100, 200 are placed in the ostium of the coronary sinus.

FIGS. 4–8 illustrate the method of use of the lead of FIG. 1 in conjunction with the guide catheter of FIG. 2. Numbered elements correspond to identically numbered elements in FIGS. 1 and 2.

Figure 4:
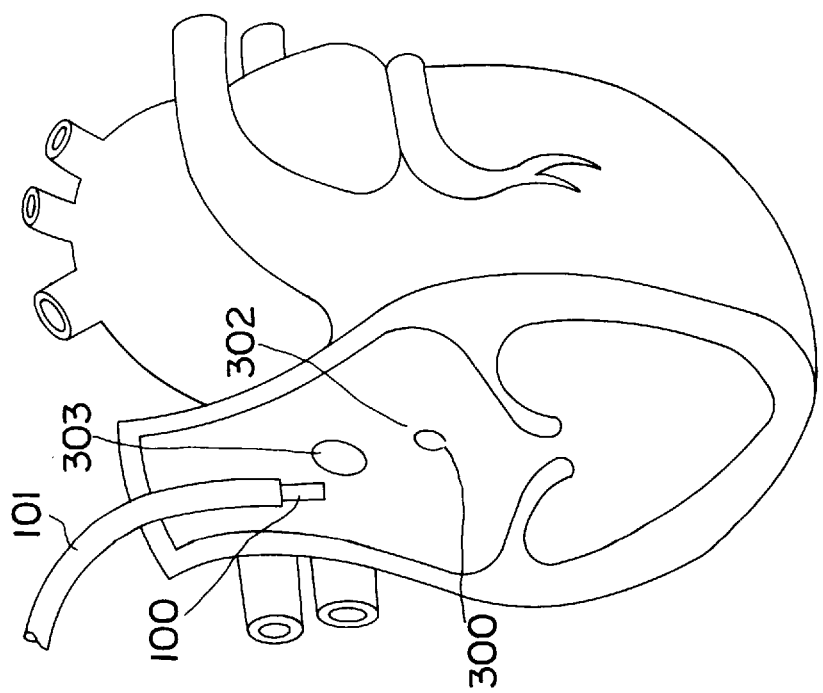
FIG. 4 illustrates the initial advancement of the guide catheter of FIG. 2 into the right atrium, prior to placement of the atrial lead.

FIG. 4 illustrates advancement of the catheter illustrated in FIG. 2 into the atrium of a human heart. The guide catheter body is advanced with tube 100 withdrawn into tube 101 to straighten both curves 105A and 105B and with the distal end of the atrial pacing lead of FIG. 1 withdrawn interior to the lateral aperture 104 on tube 100. The desired location of the electrode on the pacing lead is illustrated at 302, relative to the ostium 300 of the coronary sinus and the fossa ovale 303.

FIG. 5 shows the guide catheter with tube 100 extending distally from tube 101 to allow curve 105B to exit tube 101, providing a guide catheter with a single curve adapted to assist in locating its distal end in the ostium 300 of the coronary sinus.

Figure 6:
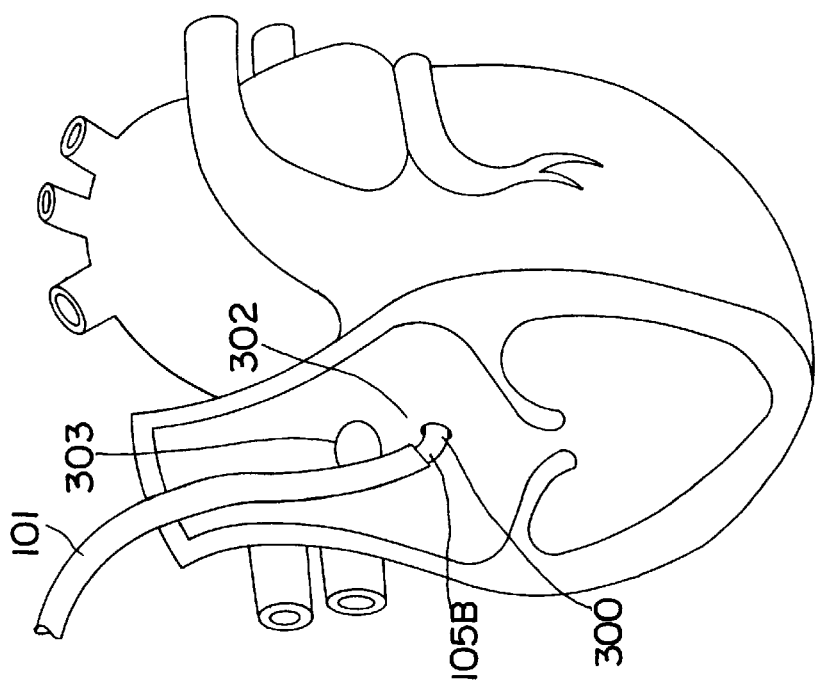
FIG. 6 illustrates the guide catheter of FIG. 2, deflected to display only the more distal of its two curves, after placement of the distal end of the guide catheter into the coronary sinus.

FIG. 6 shows the guide catheter with its distal end inserted into the ostium 300 of the coronary sinus, with curve 105B adjacent the ostium.

Figure 7:
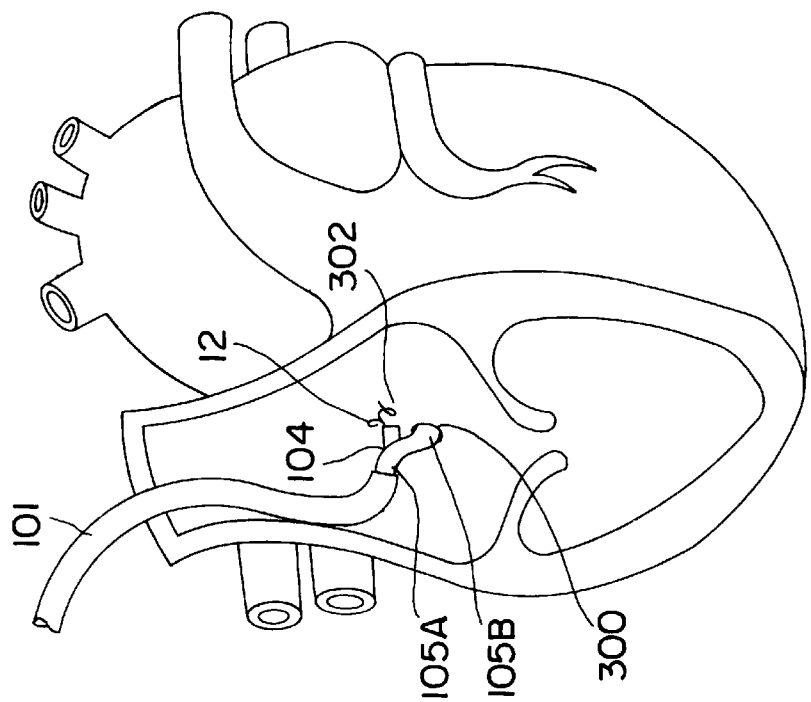
FIG. 7 illustrates the guide catheter of FIG. 2, deflected to display both of its two curves, with the distal end of the atrial pacing lead advanced from the lateral aperture into contact with the intra-atrial septum at the desired pacing site.

FIG. 7 shows catheter tube 101 withdrawn proximally to allow curve 105A to exit the tube 101, in turn placing the lateral aperture 104 adjacent the tissue of the intra-atrial septum. The distal end of lead body 10 is advanced through aperture 104 and into contact with the septum at the desired location 302. With the helical electrode located adjacent the atrial tissue, cardiac pacing and sensing thresholds can be taken. Assuming the pacing and sensing thresholds are appropriate, the lead body may be located within catheter tube 100 to screw electrode 112 into the desired location on the atrial septum. If, however, pacing and sensing thresholds are not initially adequate, the specific location of the active fixation electrode 12 may be varied by twisting the body of the guide catheter slightly, keeping the distal end of the catheter located in the ostium of the coronary sinus and/or by advancing or retracting the distal end of the catheter slightly relative to the ostium of the coronary sinus. At such point as desired pacing and thresholds are acquired, the electrode 12 may be screwed into atrial septal tissue.

Figure 8:
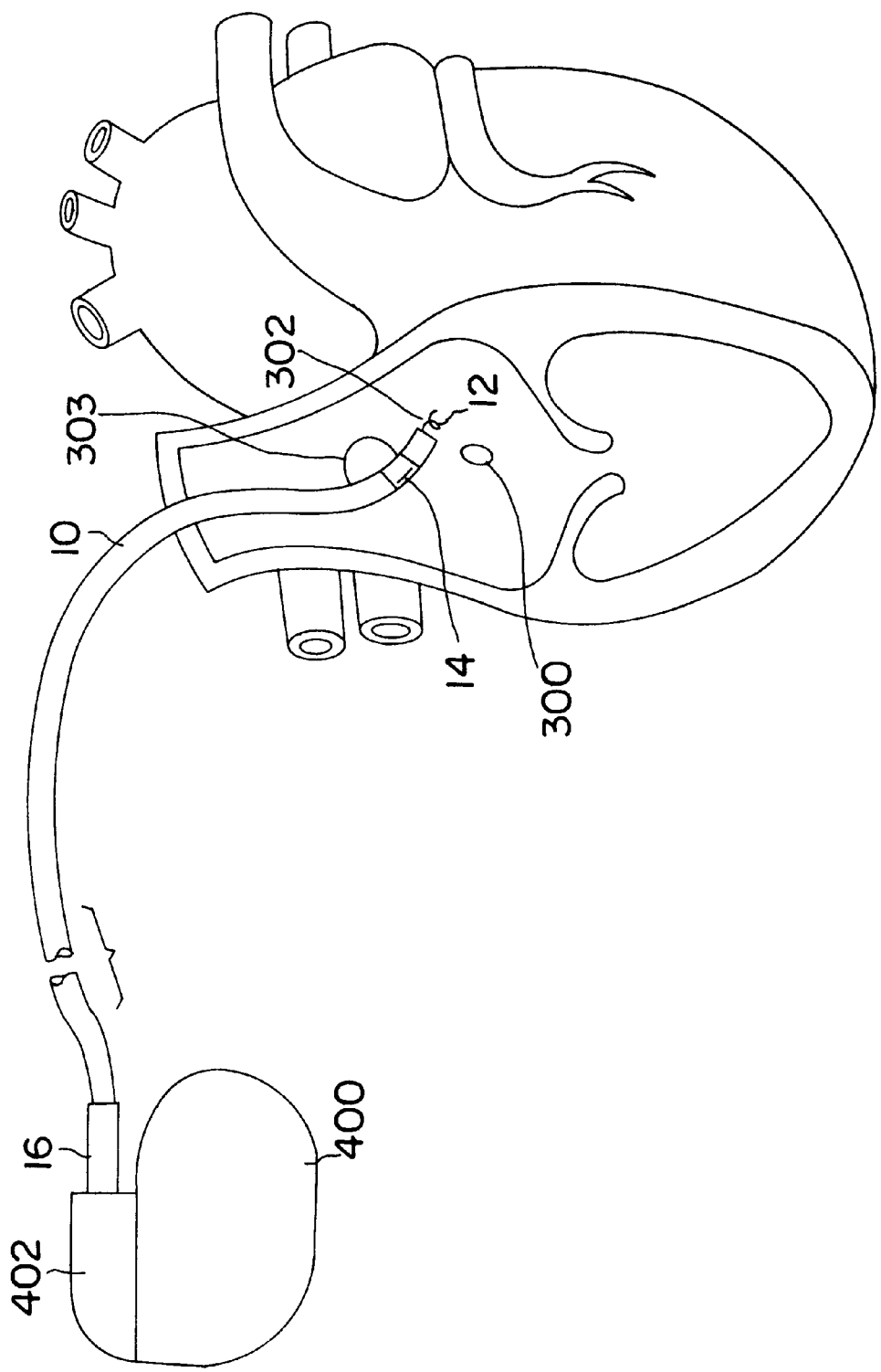
FIG. 8 illustrates the atrial lead after placement, coupled to an implantable pacemaker to allow for single electrode bi-atrial pacing.

FIG. 8 illustrates the lead of FIG. 1 as installed with electrode 12 located at the desired location 302 in the intra-atrial septum. In this location, electrical pulses provided to electrode 12 can be employed to simultaneously pace both atria The connector 16 located at the proximal end of lead body 10 is shown inserted into the connector block 402 of a cardiac pacemaker 400 which employs electrodes 12 and 14 to sense and pace the atria of the heart.

In conjunction with the above disclosure, I claim:

1. A method of implanting an atrial pacing lead, comprising:

advancing a guide catheter having a longitudinal lumen and a lateral aperture opened to the longitudinal lumen of the catheter proximal to a distal end of the catheter to the ostium of a patient's coronary sinus and inserting the distal end of the guide catheter into the coronary sinus such that the lateral aperture of the catheter is located in the patient's right atrium;

advancing an atrial pacing lead having an active fixation electrode located on a distal portion thereof through the lumen of the guide catheter such that the active fixation electrode exits the lateral aperture of the guide catheter; and affixing the electrode to tissue of the atrial septum.

2. A method according to claim 1 wherein said step of advancing said guide catheter comprises deflecting said guide catheter to display a first curve prior to inserting said guide catheter into the coronary sinus.

3. A method according to claim 1 wherein said step of advancing said guide catheter comprises, prior to advancing said atrial pacing lead, deflecting said guide catheter to display first and second oppositely directed curves located on a distal portion thereof, the second curve being proximal to the first curve and said lateral aperture located on an exterior portion of said second curve.

4. A method of implanting an atrial pacing lead, comprising:

advancing a guide catheter having a longitudinal lumen and a lateral aperture opened to the longitudinal lumen of the catheter proximal to a distal end of the catheter and deflectable to display a first curve located on a distal portion thereof, to the ostium of a patient's coronary sinus and inserting the distal end of the guide catheter into the coronary sinus such that the lateral aperture of the catheter is located in the patient's right atrium;

deflecting the guide catheter to display the first curve;

advancing an atrial pacing lead having an active fixation electrode located on a distal portion thereof through the lumen of the guide catheter such that the active fixation electrode exits the lateral aperture of the guide catheter; and affixing the electrode to tissue of the atrial septum.

5. A method according to claim 4 wherein the guide catheter comprises an inner tube formed to display the first curve and an outer tube mounted around the inner tube and wherein deflecting the guide catheter comprises advancing the inner tube out of the outer tube.

6. A method according to claim 1 or claim 4 or claim 5, wherein the active fixation electrode is a helical electrode and wherein affixing the electrode comprises screwing the electrode into tissue of the atrial septum.

7. A method according to claim 1 or claim 4 or claim 5, wherein the active fixation electrode is an electrode provided with an active fixation device and wherein affixing the electrode comprises inserting the active fixation device into tissue of the atrial septum.

8. A method of implanting an atrial pacing lead, comprising:

advancing a guide catheter having a longitudinal lumen and a lateral aperture opened to the longitudinal lumen of the catheter proximal to a distal end of the catheter and deflectable to display first and second oppositely directed curves located on a distal portion thereof wherein the second curve is proximal to the first curve and the lateral aperture is located on an exterior portion of the second curve, to the ostium of a patient's coronary sinus and inserting the distal end of the guide catheter into the coronary sinus such that the lateral aperture of the catheter is located in the patient's right atrium;

deflecting the guide catheter to display the first and second curves;

advancing an atrial pacing lead having an active fixation electrode located on a distal portion thereof through the lumen of the guide catheter such that the active fixation electrode exits the lateral aperture of the guide catheter; and affixing the electrode to tissue of the atrial septum.

9. A method according to claim 8 wherein the guide catheter comprises an inner tube formed to display the first and second curves and an outer tube mounted around the inner tube and wherein deflecting the guide catheter comprises advancing the inner tube out of the outer tube.

* * * * *